US010018461B2

(12) United States Patent
Hogan

(10) Patent No.: US 10,018,461 B2
(45) Date of Patent: Jul. 10, 2018

(54) REFERENCE SIGNAL FILTER FOR INTERFEROMETRIC SYSTEM

(71) Applicant: Joshua Noel Hogan, Los Altos, CA (US)

(72) Inventor: Joshua Noel Hogan, Los Altos, CA (US)

(*) Notice: Subject to any disclaimer, the term of this patent is extended or adjusted under 35 U.S.C. 154(b) by 0 days.

(21) Appl. No.: 15/539,945

(22) PCT Filed: Jan. 1, 2016

(86) PCT No.: PCT/US2016/012002
§ 371 (c)(1),
(2) Date: Jun. 26, 2017

(87) PCT Pub. No.: WO2016/109844
PCT Pub. Date: Jul. 7, 2016

(65) Prior Publication Data
US 2017/0370699 A1    Dec. 28, 2017

Related U.S. Application Data

(60) Provisional application No. 62/099,521, filed on Jan. 4, 2015.

(51) Int. Cl.
*G01B 9/02*    (2006.01)

(52) U.S. Cl.
CPC ..... *G01B 9/02059* (2013.01); *G01B 9/02091* (2013.01)

(58) Field of Classification Search
CPC ............ G01B 9/02091; G01B 9/02034; G01B 9/02056; G01B 9/02059
See application file for complete search history.

(56) References Cited

U.S. PATENT DOCUMENTS

| 5,675,413 | A | * | 10/1997 | Prikryl | ...................... G01J 3/45 |
| | | | | | 356/508 |
| 6,725,073 | B1 | | 4/2004 | Motamedi | |
| 7,526,329 | B2 | | 4/2009 | Hogan | |
| 7,751,862 | B2 | | 7/2010 | Hogan | |
| 8,310,681 | B2 | | 11/2012 | Hogan | |
| 2017/0153434 | A1 | * | 6/2017 | Shaked | .............. G02B 21/0056 |

* cited by examiner

*Primary Examiner* — Jonathan Hansen

(57) ABSTRACT

The invention provides a method and apparatus for applying spatial filtering the optical beam of a free space optical coherence tomography (OCT) system substantially without problematic reflections back to the optical source. The invention teaches spatially filtering the reference beam of the OCT system which is typically designed to provide isolation of the optical source from undesirable optical feed-back, thereby achieving spatial filtering without generating undesirable reflections back to the optical source. Various embodiments are taught.

8 Claims, 5 Drawing Sheets

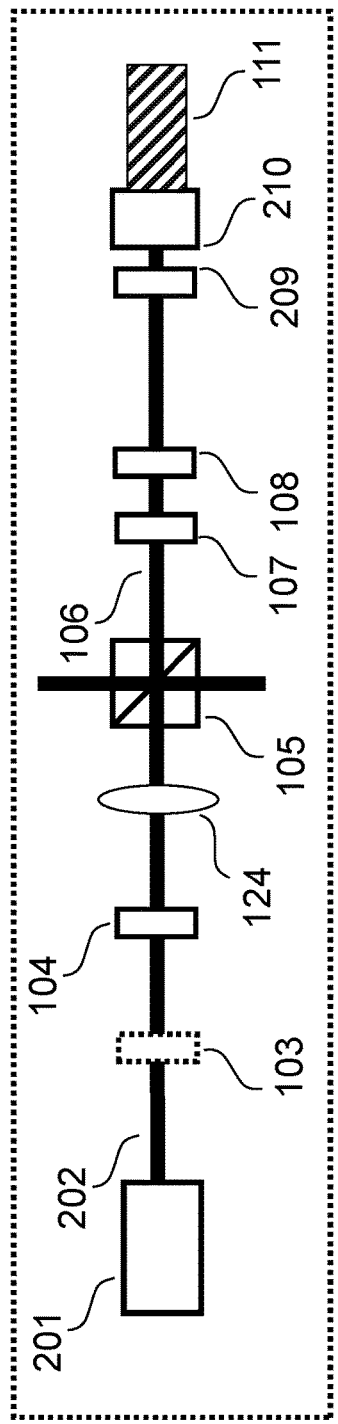
Figure 4A
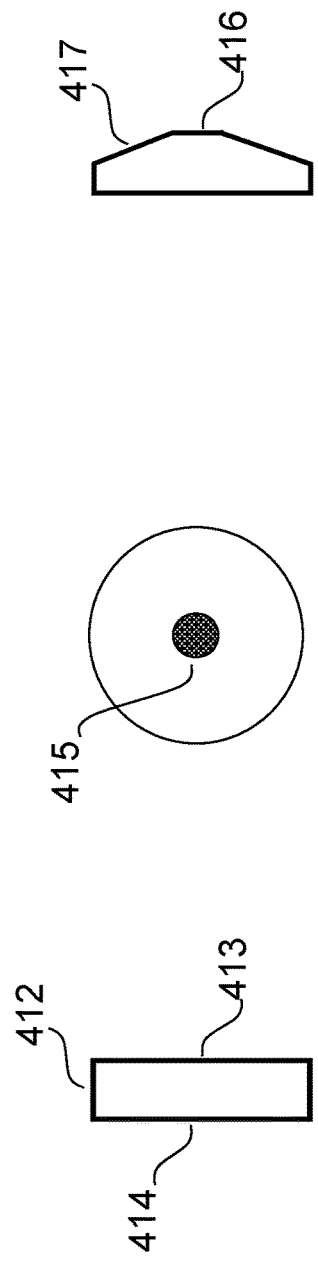
Figure 4D
Figure 4C
Figure 4B

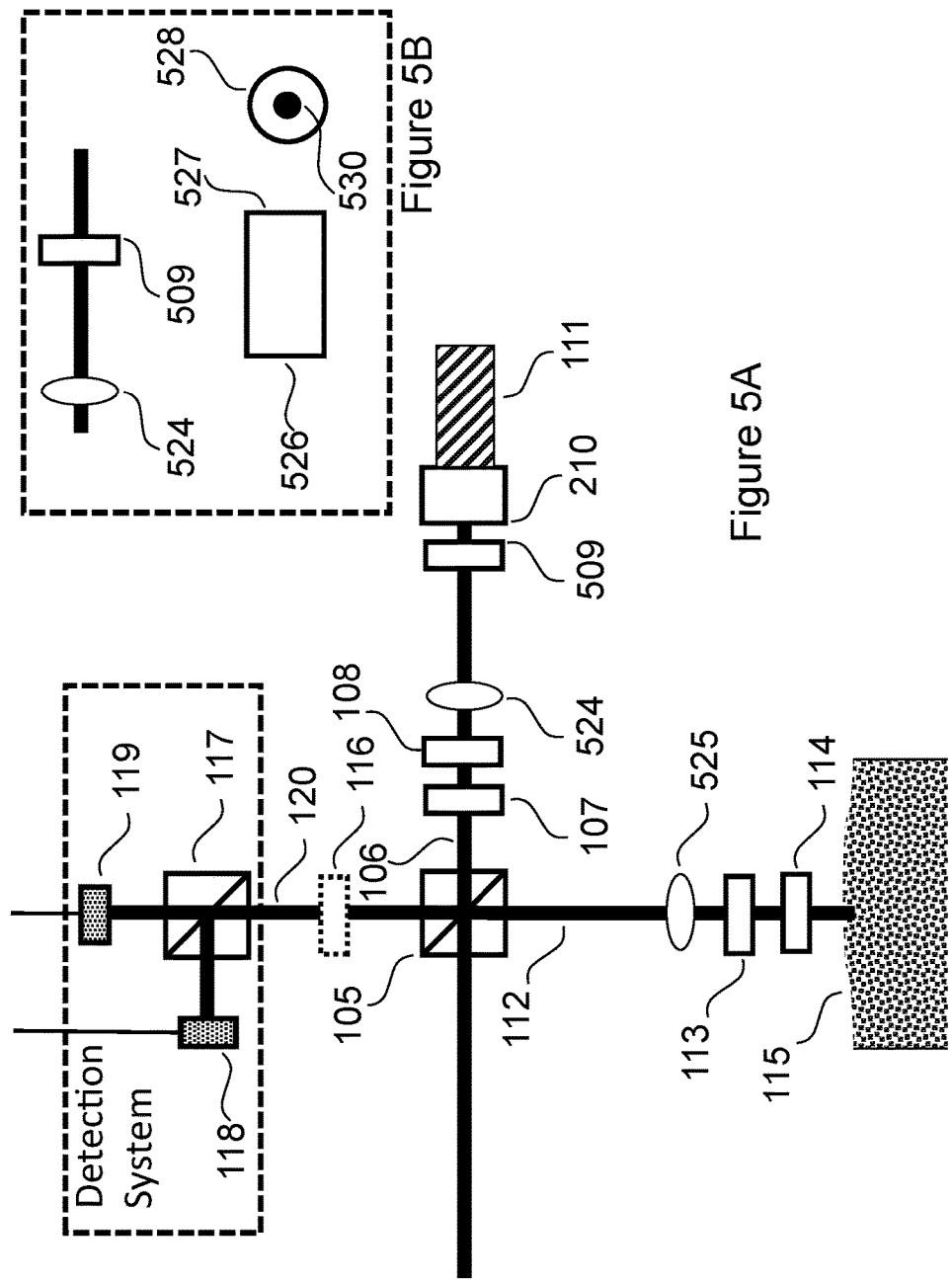

REFERENCE SIGNAL FILTER FOR INTERFEROMETRIC SYSTEM

CROSS REFERENCES TO RELATED PATENTS OR APPLICATIONS

This utility application, claim priority from U.S. provisional Patent application No. 62/099,521; this application is also related to U.S. provisional patent application Ser. No. 62/096,909 titled A polarized OCT system with improved SNR, and U.S. application Ser. No. 14/975,745 the contents of which are incorporated herein by reference as if fully set forth herein; U.S. Pat. No. 7,526,329 titled Multiple Reference Non-invasive Analysis System; U.S. Pat. No. 7,751,862 titled Frequency Resolved Imaging System; and U.S. Pat. No. 8,310,681 titled Orthogonal reference analysis system with enhanced SNR.

FIELD OF THE INVENTION

The invention described and illustrated in this application relates to the field of non-invasive imaging, analysis and measurement of targets such as tissue. Applications include, but are not limited to: imaging sub-dermal fingerprints in tissue; non-invasively analyzing tissue to measure the concentration of analytes such as the concentration of glucose in tissue or tissue fluids; measuring the thickness of particular tissue layers, such as the thickness of the layer comprised of the portion of the retina of an eye between the inner limiting membrane (ILM) and the retinal pigment epithelium (RPE). In particular the invention relates to improving the performance of the non-invasive interferometric technologies such as Optical Coherence Tomography (OCT) for imaging and analyzing tissue including, but not limited to, skin tissue and retinal tissue.

BACKGROUND OF THE INVENTION

OCT is commonly used to image tissue for ophthalmic analysis, such as retinal imaging and analysis. OCT is also used to image skin tissue and OCT has been explored as a technique for measuring glucose concentration. For example U.S. Pat. No. 6,725,073 by Motamedi, et al., titled "Methods for noninvasive analyte sensing" describes using OCT to measure glucose concentration.

An OCT system, such as the polarized multiple reference system OCT system, consistent with prior art, is depicted in FIG. 1. A broadband optical source, such as a super-luminescent diode (SLD) 101, is fiber coupled through a length of optical fiber 123 with a fiber collimator (not shown) and emits a collimated optical beam 102 which is transmitted through an optional polarizer 103 through a half-wave plate 104 and split by a polarized beam-splitter 105 into reference radiation 106 and probe radiation 112. The length of optical fiber 123 acts as a spatial filter to filter the optical radiation and thereby improve the quality of interference signals.

The reference radiation 106 is transmitted through an attenuator 107 and a quarter wave plate 108 and then partially through a partial reflective mirror 109 to a reference mirror 110 mounted on a oscillating translation device 111, such as a voice coil or piezo device. The combination of the partial mirror 109 and the reference mirror 110 generates multiple reference signals as described in the patents incorporated herein by reference.

As the reflected reference radiation is transmitted back through the quarter wave plate 108, its polarization vector is rotated such that it will be re-directed by the polarized beam-splitter 105 towards the detection system depicted in the dashed box of FIG. 1.

The probe radiation 112 is transmitted through a second quarter wave plate 113 and through an anti-reflection coated blank that compensates for effects of the optical elements in the reference path. The probe radiation 112 is scattered by components in the target 115. Some of the probe radiation is scattered back through the quarter wave plate 113 where the double pass through the quarter wave plate 113 rotates its polarization vector by ninety degrees thereby enabling this scattered probe radiation to be transmitted through the polarized beam-splitter 105 towards the detection system.

The combined scattered probe radiation and reflected reference radiation is transmitted through an optional second half wave plate 116 to a second polarized beam splitter 117 that reflects one set of components of the reflected reference and scattered probe radiation to a detector 118 and transmits the orthogonal set of components of the reflected reference and scattered probe radiation to a detector 119 thereby achieving balanced detection.

In some embodiments the optional second half wave plate 116 is not present but the second polarized beam splitter 117 is rotated forty five degrees about the optical beam 120 so that again the polarized beam splitter 117 reflects one set of components of the reflected reference and scattered probe radiation to a detector 118 and transmits the orthogonal set of components of the reflected reference and scattered probe radiation to a detector 119.

Operation of the OCT system is controlled by means of a control module 121. The detected signals are processed by a processing module 122 to yield imaging and analysis of the target. The OCT system typically includes one or more lens to focus the reference and probe radiation. In the embodiment depicted in FIG. 1 a single lens 124 focuses both the reference and the probe radiation. Such systems also typically include one or more detector lenses.

In the embodiment depicted, the broadband optical source, such as a super-luminescent diode (SLD) and lens combination 101, that emits the collimated optical beam 102 includes a fiber that couples the SLD, via a fiber collimator that delivers the collimated beam to the rest of the optical system. In such fiber coupled systems the fiber acts as a spatial filter that delivers a high quality collimated beam. In fiber based OCT systems, (in contrast to free space OCT systems) the beam splitter function is also typically accomplished in fiber and there is therefore extensive fiber based spatial filtering.

However, in free space based OCT systems without fiber coupling between the SLD source and the collimated beam, the lack of spatial filtering degrades the performance of the OCT system. Approaches to accomplish spatial filtering by focusing the output of the SLD through a pin-hole, in addition to adding complexity, have the undesirable consequence of reflecting light back to the SLD which can cause unacceptable noise related problems.

An optical isolator, typically using polarization components, can be installed between the SLD source and the pin-hole to substantially reduce undesirable light reflected back from the pin-hole to the SLD. However, this approach requires additional optical components with associated cost and complexity.

While fiber based OCT systems have the advantage of fiber spatial filtering of the optical beam, free space OCT systems have the significant advantage of being potentially very low cost and thereby offering significant commercial advantage. There is therefore an unmet need for a free space OCT system that has spatial filtering without the undesirable reflections back to the SLD and without the need for additional optical components.

BRIEF SUMMARY OF THE INVENTION

The invention described herein provides a method and apparatus for applying spatial filtering to the optical beam of a free space optical coherence tomography (OCT) system substantially without problematic reflections back to the optical source. The invention provides spatially filtering the reference beam of an OCT system. The spatially filtered reference beam only forms interference signals with the portion of probe radiation corresponding to the spatially filtered reference beam, thereby effectively spatially filtering complete interference signals. Undesirable reflections due to spatially filtering the reference beam also benefit from OCT designs that provide isolation of the optical source from undesirable optical feedback thereby achieving spatial filtering without generating undesirable reflections back to the optical source.

The invention provides an improved free space optical coherence tomography system. In a system including a radiation source, at least one probe beam and one reference beam, the inventive system provides that the reference beam is spatially filtered, so that a portion of the spatially filtered reference beam forms at least one interference signal with a portion of the probe radiation that corresponds to a portion of the spatially filtered reference beam, thereby effectively spatially filtering the resulting interference signal.

The reference beam is spatially filtered by focusing the reference beam onto a surface that is reflective at a predetermined region and where that region has a diameter that is substantially less than the diameter of the collimated beam and is typically within a range of approximately equal to one to four times the dimension of the waist of the focused reference beam.

In the preferred embodiments, the region is partially reflective, with reflectivity in the range of 80-95%.

In alternate embodiments, the partially reflective surface is a surface of a gradient index lens.

In other embodiments, the surface having a predetermined region of reflectivity is that of the reference mirror. The region has a diameter within a range of approximately equal to one to four times the dimension of the waist of the focused reference beam. In some of these embodiments, such as Fourier domain OCT or conventional domain OCT, there is no partial mirror.

In alternate embodiments, in addition to the reference mirror region of reflectivity, an additional or second surface also having a predetermined region of reflectivity in the range of 80-95% and having a diameter within a range of approximately equal to one to four times the dimension of the waist of the focused reference beam, is oriented to receive reflections from the reference mirror surface.

In one embodiment, the invention provides an improved free space optical coherence tomography system, where the system includes, among other necessary components, a radiation source producing reference and probe radiation, a detector, a pathway for reference radiation where said pathway includes a partial mirror (reflecting in the range of 80-95 percent), a reference mirror, a pathway for probe radiation, a means for capturing and processing interferometric signals formed by reference and probe radiation and received at the detector, and the improvement comprises the partial mirror having a preselected region of its reflecting surface so that radiation reflected between the preselected region of the partial mirror and the reference mirror is selected, and substantially all other radiation is filtered out of the reference signal.

The preselected region of the partial mirror has a diameter within a range of approximately equal to one to four times a value of the waist dimension of the focused reference beam.

Alternatively, in an embodiment providing an improved free space optical coherence tomography system, where the system includes all functional components including a radiation source producing reference and probe radiation, a detector, a pathway for reference radiation, a reference mirror, a pathway for probe radiation, a means for capturing and processing interferometric signals formed by reference and probe radiation and received at the detector, the improvement comprises the reference mirror having a preselected region of its reflecting surface so that radiation reflected from the preselected region is selected, and substantially all other radiation is filtered out of the reference signal. The preselected region has a diameter within a range of approximately equal to one to four times a value of the waist dimension of a focused reference beam.

Various other embodiments are included in the invention, either depicted in the drawings or discussed in the detailed description.

BRIEF DESCRIPTION OF THE DRAWINGS

Drawings intended as an aid to understanding the invention are:

FIG. 4, 4A through 4D inclusive, is an illustration of the modified partial mirror optic depicting a reduced area reflective surface and optional angled aspects of the partial mirror optic.

FIGS. 5, 5A and 5B inclusive, depicts an alternate embodiment according to the invention.

DETAILED DESCRIPTION OF A PREFERRED EMBODIMENT OF THE INVENTION

The invention described herein provides a method, apparatus and system for spatially filtering the reference beam of an interferometric optical system such as an optical coherence tomography (OCT) system and thereby improving the signal to noise ratio of the associated interference signals. Since the spatially filtered reference beam forms an interference signal only with the portion of probe radiation that corresponds to a spatially filtered portion of the reference beam, spatially filtering the reference beam thereby effectively spatially filters the interference signal.

Figure 1:
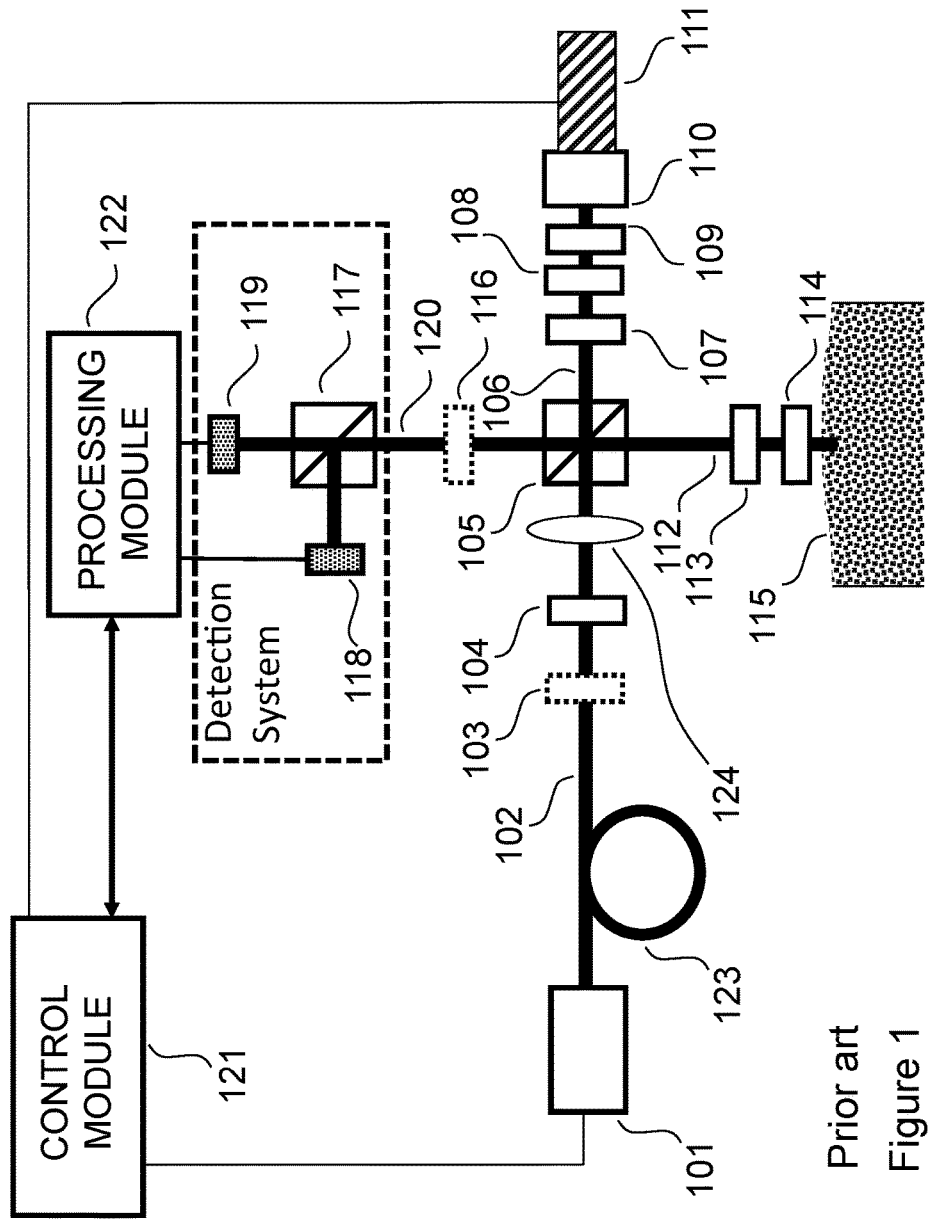
FIG. 1 is an illustration of prior art depicting an OCT system using a length of fiber to spatially filter the optical beam.

FIG. 1 has been discussed previously herein.

Figure 2:
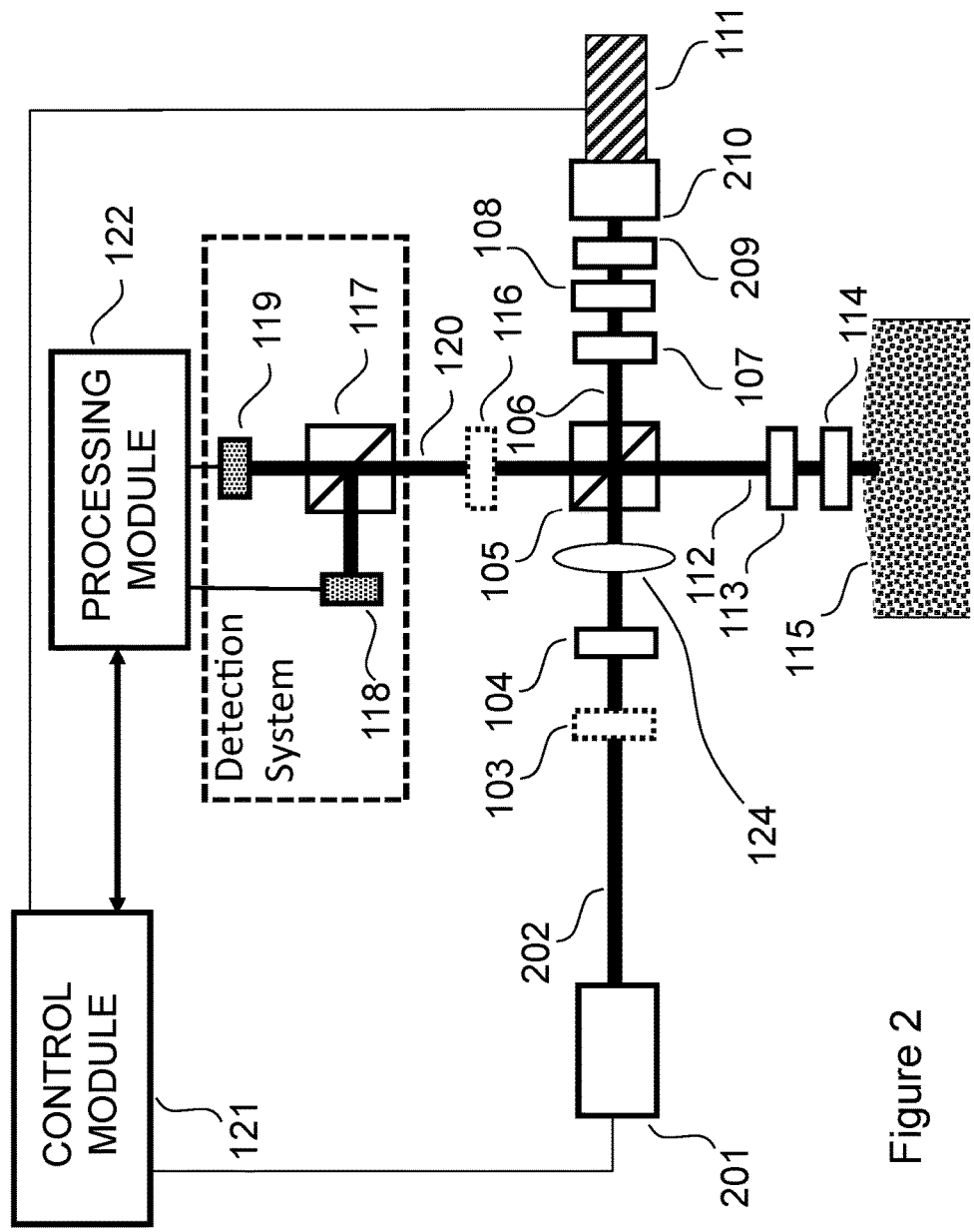
FIG. 2 is an illustration of an embodiment of the invention depicting a free space OCT system that uses a single lens to focus both the reference beam and the probe beam.

A preferred embodiment is depicted in FIG. 2 and, is in many respects the same as the system depicted in FIG. 1 (as indicated by the same numbering). However the partial mirror 209 and optionally the reference mirror 210 are different and are described in more detail in FIG. 4. Also the optical source 201 that outputs a collimated optical beam 202 is a free space configuration and is depicted in more detail in FIG. 3.

Figure 3:
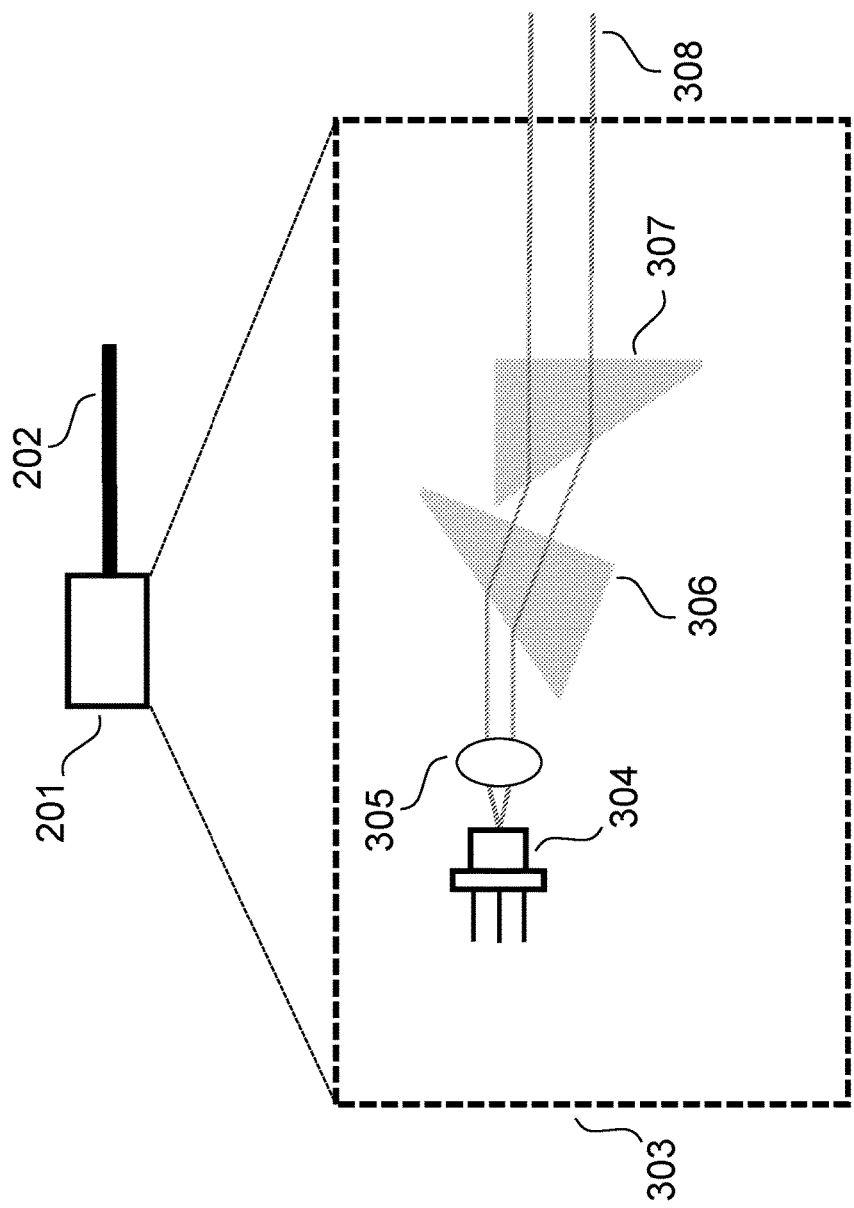
FIG. 3 is an illustration of both a typical approach to collimation and conditioning of the optical beam emitted by the optical source.

The dashed box 303 of FIG. 3 depicts an SLD 304 in a TO can (a transistor outline can)—(or, alternatively, a chip level device) whose optical output is collimated by a lens 305 which is typically an aspheric lens (or, alternatively, a lens system). In alternate embodiments, the collimated beam is made round by an anamorphic pair of prisms 306 and 307 to output a collimated and round beam 308 (which corresponds to 202 of FIG. 2).

In FIG. 4A of sheet 4 the reference path of FIG. 2 is again shown and the optic element that contains the partial mirror 209 (of FIG. 2) is depicted in more detail in FIGS. 4B, 4C and (optionally) 4D. The optic element 412 has a partial mirror surface or coating 413 on one side. In the preferred embodiment, the partially reflective mirror should have a reflectivity in the range of 80% to 95%. The other surface 414 may be anti-reflection coated, uncoated or coated for a specific reflectivity (depending on the embodiment).

FIG. 4C depicts a key aspect of the present invention. FIG. 4C depicts an end on view of the partial mirror surface 413 of FIG. 4B and shows that the partial mirror is confined to a small region 415, typically at the center and typically (though not necessarily) round. The optimal magnitude of this predetermined partially reflecting region 415 is dependent on the beam waist of the optical beam focused by the lens 124.

The diameter of the waist of the focused beam depends on the diameter of the collimated beam and the focal length of the focusing lens. In typical applications the diameter of the waist of the focused beam is 20 to 50 microns. Accordingly, the diameter of the predetermined reflective region 415 is typically 20 to 60 microns. FIG. 4D shows the same view of the optic as FIG. 4B and shows the optional angled profile 417 of the surface that does not contain the predetermined partially reflecting region 416 (similar to region 415 of FIG. 4C). The angled profile directs radiation that is not on the path to the reflective region 415 out of the optical system and thereby prevents such radiation from generating noise.

In alternate embodiments the lens 124 is a holographic lens.

In some embodiments the single lens 124 that focuses both the reference and the probe radiation is replaced by two lenses. FIG. 5A depicts a sub-set of the system of FIG. 2 where the single lens 124 of FIG. 2 is replaced by lens 524 in the reference path and by lens 525 in the probe path. In some embodiments one lens is a gradient index lens; in alternate embodiments, both of the lenses are GRIN (gradient index) lenses.

The effect of having a reduced sized partial mirror is that it effectively behaves as a pinhole and thereby spatially filters the reference beam. In the preferred embodiment, the radiation that is not part of the spatially filtered reference radiation is substantially prevented from being propagated back to the optical source by the techniques described in U.S. provisional patent application No. 62/096,909 (that is incorporated herein by reference).

FIG. 4D depicts an alternate embodiment providing an angled version of the optic 412 where the partial mirror 416 is a flat surface, while the rest of that side of the optic is angled, as indicated by 417. The angled optic directs unwanted radiation out of the optical system so it cannot generate noise.

In some embodiments, depicted in FIG. 5B of Sheet 5, where the single lens 124 (of FIG. 2) is replaced by a reference path lens 524 and a probe path lens 525, the reference path lens 525 and the partial mirror 525 are replaced by a GRIN (gradient index) lens 526 with the reduced area partially reflective element 530 on a face 528 of the GRIN lens where the size and location of the reduced area partially reflective element are such that only desired reference radiation is reflected by the reduced area partially reflective element, thereby spatially filtering the reference radiation. An advantage of this embodiment is that the reduced area partially reflective element is physically fixed at a location in the waist of the focused beam and thereby less sensitive to component alignment.

In other embodiments the optic with the reference mirror 210 contains the reduced area reflective region and in some embodiments the rest of the reference mirror optic is also angled, similar to that depicted in FIG. 4D. In some embodiments, this modification to the reference mirror 210 is an alternative to the similar modification to the partial mirror 209, 413; in further embodiments, both the partial mirror and the reference mirror have preselected regions of reflectivity where the reflectivity is of 80-95% in the case of the partial mirror and a reflectivity of approximately 100% in the case of the reference mirror. Typically the reduced area reflective element (either partial or full mirror) is round in shape, however, other shapes, such as oval are preferred in some embodiments.

While the preferred embodiment has been described with respect to a polarized version of a multiple reference OCT system, the invention can be applied to any free space OCT system (polarized or non-polarized), or indeed to any free-space interferometric system. In the cases of Fourier domain OCT, conventional time domain OCT or full field OCT, none of which require a partial mirror, the reference mirror contains the reduced area reflective element.

The invention is generally applicable to free space OCT system, and provides a spatially filtered reference beam and wherein a portion of the spatially filtered reference beam forms at least one interference signal with only that portion of probe radiation that corresponds to the portion of the spatially filtered reference beam, thereby effectively spatially filtering the resulting interference signal.

In the preferred embodiment the reduced area reflective surface acts as an effective (or reflective) pinhole. In other embodiments one or more actual pinholes are used to spatially filter the reference beam. Such pinholes have a diameter of 20 to 60 microns. In some embodiments the reference beam is focused into a pinhole that only transmits a small round portion of the waist of the focused reference beam thereby spatially filtering the reference beam.

Spatially filtering only the reference beam enables availing of techniques to isolate the optical source from undesirable noise generating optical feedback that are described in U.S. provisional patent application No. 62/096,909 titled "A polarized OCT system with improved SNR", the contents of which are incorporated herein by reference.

In some embodiments the reference beam is spatially filtered by focusing the reference beam onto a reflective surface that is reflective only at a small region related to the waist of the focused beam.

In embodiments where the surface having a predetermined reflective region, and where the reflective region size is related to the waist of the focused beam, it 415 is a partially reflective surface, typically between 80 and 95% reflective. In some embodiments the partially reflective surface 415 is a surface 413 of a GRIN lens; alternatively, the surface having a predetermined reflective region is a reference mirror surface 210.

Numerous modifications and variations could be made—by those skilled in the art—within the spirit and scope of the invention; therefore to be understood that within the scope of the claims, the invention may be practiced otherwise than as specifically described herein.

I claim:

1. A free space optical coherence tomography system, said system including a radiation source, where said source produces at least one probe beam and one reference beam, wherein said reference beam of said optical coherence tomography system is spatially filtered, and wherein a portion of said spatially filtered reference beam forms at least one interference signal with a portion of said probe radiation that corresponds to said portion of said spatially filtered reference beam, thereby effectively spatially filtering the resulting interference signal, wherein said reference beam is spatially filtered by focusing said reference beam onto a surface, wherein said surface is reflective at a predetermined region of said surface and where said region has a diameter within a range of approximately equal to one to four times the dimension of the waist of the focused reference beam.

2. The system of claim 1, wherein said predetermined region of said surface is a partially reflective surface, where said surface reflectivity is in the range of 80 to 95 percent.

3. The system of claim 2, wherein said partially reflective surface is a surface of a gradient index lens.

4. The system of claim 1, wherein said surface that is reflective at a predetermined region of said surface is a reference mirror surface.

5. The system of claim 4, further including, a second surface having a predetermined region of reflectivity in the range of 80 to 95 percent and where said region has a diameter within a range of approximately equal to one to four times the dimension of the waist of the focused reference beam, and where said second surface is oriented to receive reflections from said reference mirror surface.

6. An improved free space optical coherence tomography system, said system including a radiation source producing reference and probe radiation, a detector, a pathway for reference radiation where said pathway includes a partial mirror, which said partial mirror reflects in the range of 80 to 95 percent, a reference mirror, a pathway for probe radiation, a means for capturing and processing interferometric signals formed by reference and probe radiation and received at the detector, said improvement comprising:

said partial mirror having a preselected region of its reflecting surface so that radiation reflected between said preselected region of said partial mirror and said reference mirror is selected, and substantially all other radiation is filtered out of the reference signal.

7. The system of claim 6, wherein said preselected region of said partial mirror has a diameter within a range of approximately equal to one to four times a value of the waist dimension of a focused reference beam.

8. An improved free space optical coherence tomography system, said system including a radiation source producing reference and probe radiation, a detector, a pathway for reference radiation, a reference mirror, a pathway for probe radiation, a means for capturing and processing interferometric signals formed by reference and probe radiation and received at the detector, said improvement comprising:

said reference mirror having a preselected region of its reflecting surface so that radiation reflected from said preselected region is selected, and substantially all other radiation is filtered out of the reference signal, and wherein said preselected region of said reference mirror has a diameter within a range of approximately equal to one to four times a value of the waist dimension of a focused reference beam.

* * * * *